(12) United States Patent
Zehner et al.

(10) Patent No.: US 6,894,193 B2
(45) Date of Patent: May 17, 2005

(54) METHOD FOR HYDROGENATING LIQUID ORGANIC COMPOUNDS

(75) Inventors: Peter Zehner, Ludwigshafen (DE); Oliver Bey, Niederkirchen (DE); Gunter Georgi, Lauchhammer (DE); Jörn Müller, Bad Essen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 54 days.

(21) Appl. No.: 10/470,236

(22) PCT Filed: Jan. 25, 2002

(86) PCT No.: PCT/EP02/00766

§ 371 (c)(1),
(2), (4) Date: Jul. 2, 2003

(87) PCT Pub. No.: WO02/062729

PCT Pub. Date: Aug. 15, 2002

(65) Prior Publication Data

US 2004/0073066 A1 Apr. 15, 2004

(30) Foreign Application Priority Data

Feb. 2, 2001 (DE) .......................... 101 05 277

(51) Int. Cl.$^7$ .......................... C07B 43/04; C07B 31/00; C07C 209/32
(52) U.S. Cl. ...................... 564/420; 564/421; 564/422; 564/423; 564/417; 564/418
(58) Field of Search ................................. 564/417, 418, 564/420–423

(56) References Cited

U.S. PATENT DOCUMENTS

| 4,067,905 A | | 1/1978 | Adrian et al. |
| 4,256,671 A | * | 3/1981 | Hildreth et al. ............. 564/422 |
| 4,717,774 A | | 1/1988 | Narayan et al. |
| 5,387,396 A | | 2/1995 | Dallmeyer et al. |
| 5,563,296 A | | 10/1996 | Zarnack et al. |
| 6,350,911 B1 | | 2/2002 | Sander et al. |

FOREIGN PATENT DOCUMENTS

| CA | 1211757 | 9/1986 |
| DE | 26 03 076 | 8/1976 |
| DE | 41 02 860 | 1/1991 |
| EP | A 124 010 | 11/1984 |
| EP | A 263 935 | 4/1988 |
| EP | A 634 391 | 1/1995 |
| HU | 63606 | 9/1993 |
| RU | 2081111 | 6/1997 |
| WO | WO 87/07598 | 12/1987 |
| WO | WO 97/30967 | 8/1997 |
| WO | WO 00/35852 | 6/2000 |

OTHER PUBLICATIONS

PCT International Report Dated Jun. 25, 2002.

* cited by examiner

*Primary Examiner*—Brian J. Davis
(74) *Attorney, Agent, or Firm*—Fernando A. Borrego

(57) ABSTRACT

Liquid organic compounds are hydrogenated by a process in which the hydrogen present in the reactor contains proportions of at least one gas which is inert in the hydrogenation reaction.

14 Claims, No Drawings

METHOD FOR HYDROGENATING LIQUID ORGANIC COMPOUNDS

This application is a 371 of PCT/EP02/00766 filed Jan. 25, 2002.

The present invention relates to a process for hydrogenating liquid organic compounds, in particular for hydrogenating nitro compounds to give amines.

The hydrogenation of liquid organic compounds is one of the most frequent processes in the chemical industry. An industrially important hydrogenation reaction is the hydrogenation of nitro compounds to give the corresponding amines.

In hydrogenations of this type, the hydrogenation of nitroaromatics to aromatic amines is particularly important. Aromatic amines can be widely used. For example, aniline is the starting material for many organic syntheses. Tolylenediamine, frequently referred to as TDA, can be reacted with phosgene to give tolylene diisocyanate, one of the isocyanates most frequently used for the preparation of polyurethanes.

The catalytic hydrogenation of liquid starting materials is carried out in industry predominantly using a finely suspended catalyst or in a fixed bed. The reactors used may be autoclaves, loop reactors, stirred kettles, bubble columns or reactor cascades. Such processes are described, for example, in EP-A-263 935, EP-A-634 391, EP-A-124 010 or WO 00/35852.

Since the solubility of hydrogen in the liquid phase is generally very low, the processes known in industry are operated under pressure in order to increase the saturation concentrations of the hydrogen. The gaseous hydrogen is frequently introduced at the bottom of the reactors and dispersed by means of stirrers, nozzles or during flow through packings, in order to achieve a large specific exchange surface between the gaseous and the liquid phase.

However, the disadvantage is that the system comprising hydrogenation bath and hydrogen exhibits strong coalescence, i.e. relatively large bubbles are formed again immediately after leaving the dispersing zone and substantially reduce the specific exchange surfaces and hence the mass transfer. This behavior is in contrast to the prevailing opinion that coalescence is predominantly inhibited in a multimaterial mixture, such as the hydrogenation bath, and the properties of the gas have a negligible influence on the coalescence behavior.

The hydrogen which is used for the hydrogenation and is usually produced industrially in synthesis gas plants generally has a purity of more than 99.95% by volume. This is intended to ensure that a very small amount of inert gases are entrained into the hydrogenation reactors.

An advantage of the procedure using very pure hydrogen is the continuously high hydrogen partial pressure in the gas phase of the reactor, which facilitates the transfer from the gas phase into the liquid hydrogenation bath.

Furthermore, it is possible to ensure that only a small amount of the hydrogen fed to the reactor has to be discharged from the reactor as waste gas.

In general, in the processes customary in industry, from about 1 to 2% of the hydrogen introduced into the reactor are discharged as waste gas so that the gaseous byproducts and the small amounts of inert substances are removed from the reaction mixture. However, as a result of this, the purity of hydrogen in the waste gas stream generally does not fall below 98% by volume.

In the prior art processes, the high partial pressure in the reactor cannot be utilized because of the coalescence described above at the high purity of the hydrogen. The inadequate exchange surface between liquid and gaseous phases therefore results in increased aging of the catalyst and insufficient selectivity of the reaction, since the saturation concentrations of the hydrogen in the hydrogenation bath cannot be reached.

It is an object of the present invention to provide a process for hydrogenating liquid organic compounds, in particular for hydrogenating nitro compounds to amines, in which optimum mass transfer between the hydrogen and the hydrogenation bath takes place, the aging of the catalyst is suppressed and the selectivity of the reaction is increased.

We have found that this object is achieved and that, surprisingly, in the case of a mixture of the hydrogen used for the hydrogenation with proportions of at least one gas which is inert in the hydrogenation reaction, there is greater inhibition of coalescence and the mass transfer of the hydrogenation reactor can be substantially increased.

The present invention accordingly relates to a process for hydrogenating liquid organic compounds, in particular for the preparation of amines by hydrogenating the corresponding nitro compounds, wherein the hydrogen used contains proportions of at least one gas which is inert in the hydrogenation reaction.

The proportion of the gas which is inert in the hydrogenation reaction in the gas phase of the reaction is preferably from 3 to 50% by volume, based on the amount of gas in the reaction mixture. In principle, it is also possible to work outside these limits. In the case of contents below this range, however, troublesome coalescence of the gas in the liquid phase still occurs. In the case of contents above this range, the concentration of dissolved hydrogen in the hydrogenation bath may decrease owing to the low partial pressure of the hydrogen, in spite of the larger exchange surface, with the result that the yield of the reaction decreases. The content of inert gases is preferably from 3 to 30, particularly preferably from 5 to 20, % by volume, based in each case on the amount of gas in the reaction mixture.

The gases which are inert in the hydrogenation reaction must be heavier than hydrogen. In principle, all substances which are gaseous under the hydrogenation conditions and are inert in the reaction can be used for the novel process. Examples of possible gases are nitrogen, noble gases, in particular neon, argon or krypton, ammonia, lower saturated hydrocarbons, in particular methane, ethane, propane or butane, and carbon dioxide. Nitrogen is of most importance here since it can be handled safely and without problems and is generally available in sufficient quantities in industrial plants. Under certain reaction conditions, steam may also act as the gas which is inert in the hydrogenation reaction. Some of the water forms during the hydrogenation, but water may also enter the reactor with the reaction components or as a solvent. In principle, however, preferred inert substances are those which cannot condense under the conditions prevailing in the reactor, in order to avoid pressure variations or varying compositions of the gas phase.

The gases which are inert in the hydrogenation reaction can be fed to the reactor as a mixture with the hydrogen. However, it is also possible to feed it in a separate stream to the reactor.

In a further embodiment of the invention, the concentration of the gases which are inert in the hydrogenation reaction is established solely by regulating the waste gas stream. By throttling the waste gas stream from the reactor, the concentration in the reactor of the gases which are inert in the hydrogenation reaction can be established within the preferred range.

The generally used hydrogenation reactors, such as autoclaves, bubble columns, stirred kettles, loop reactors or fixed-bed reactors, generally provide good back-mixing on the gas side through specific gas recycling or through the reintroduction (redispersion) of gas from the gas phase by means of driving jets or stirrers. The waste gas stream, which as a rule is removed directly from the gas phase of the reactor, will therefore generally have the same composition as the gas circulating in the reactor.

Owing to the substantially complete back-mixing of the gas phase in the reactor, the desired concentration of hydrogen in the reactor can be established by specifying the amount of gas in this embodiment of the novel process. If the concentration of the fresh hydrogen is 99.95% by volume, the proportion of inert gases in the gas phase of the reactor is at least 5% by volume, based on the gas phase of the reactor, at a discharge rate of 1%, based on the fresh gas. If a discharge is reduced to 0.25%, based on the fresh gas, it is even possible for at least 20% by volume of inert gases to accumulate in the reactor. As stated above, substantially higher proportions of inert gases are however no longer expedient, owing to an excessive decrease in the hydrogen partial, pressure.

When regulating the concentration of the hydrogen in the reaction mixture, by establishing the amount of waste gas, the lower limit of the concentration of the hydrogen fed in should therefore be 98% by volume. In this case, with a discharge rate of 10%, based on the fresh gas, a proportion of about 20% by volume of inert gas can be established in the reactor. At lower discharge rates, the proportion of inert gas increases above the particularly preferred values; at higher discharge rates, the process may become uneconomical since excessively large amounts of hydrogen have to be removed as waste gas. In principle, the novel proportion of inert gas in the gas phase of the reactor can also be established when the fresh hydrogen has purities of more than 99.95% by volume. However, the amount of waste gas or the discharge rate must then be greatly reduced. Regulation of such small waste gas streams may be problematic in practice. In this way, however, a proportion of 5% by volume of inert gas in the gas phase of the reactor can be established at an exemplary purity of the fresh hydrogen of 99.99% by volume by reducing the discharge rate to 0.2%.

In order to achieve the desired concentration of the hydrogen, it is also possible in principle to close the waste gas valve completely and to open it discontinuously only when a specific proportion of inert gas is exceeded.

The novel process is particularly advantageous in the case of hydrogenations in which water of reaction is produced and which are operated at below 150° C.

The advantage of a hydrogenation at above 150° C. is a higher vapor pressure of the water of reaction produced in the hydrogenation, which water then likewise acts as a gas which is inert in the hydrogenation reaction, with the result that the accumulation of other inert substances in the reactor can be reduced or is no longer necessary. However, a hydrogenation at above 150° C. has disadvantages, for example accelerated catalyst aging and a higher level of byproduct formation. Temperatures above 150° C. are therefore not preferred for the novel process.

The fresh hydrogen can be fed into the gas phase of the reactor. This is advantageous particularly in the case of flow reactors, as described, for example, in EP 634 391 or WO 00/35852. In this case, however, a short-circuit with the waste gas line must be ruled out.

The fresh hydrogen is preferably metered into the liquid phase of the reactor. The introduction can be effected by means of known metering elements. Possibilities include, for example, the introduction via one or more ring lines in the liquid phase, one or more inlet pipes in the liquid phase, in particular at the bottom of the reactor, or, in the case of stirred kettles, via a hollow-shaft stirrer.

The waste gas is generally removed at the top of the reactor, via the gas phase. As stated above, it must be ensured that no short circuit to the fresh hydrogen occurs during removal of the waste gas, in order to avoid additional losses of hydrogen.

The novel process can be used in principle for all hydrogenations of organic compounds which are liquid under the reaction conditions. Examples of these are the hydrogenation of benzene to cyclohexane, of butynediol to butanediol and of oxo aldehydes to the oxo alcohols. No water of reaction is formed in any of these processes, making the presence of inert gases particularly important. The novel process can be particularly advantageously used for the preparation of amines from the corresponding nitro compounds, in particular of aromatic amines from the corresponding aromatic nitro compounds.

Aromatic nitro compounds having one or more nitro groups and 6 to 18 carbon atoms, for example nitrobenzenes, such as o-, m- and p-nitrobenzene and 1,3-dinitrobenzene, nitrotoluenes, such as 2,4- and 2,6-dinitrotoluene and 2,4,6-trinitrotoluene, nitroxylols, such as 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes, such as 1- and 2-nitronaphthalene and 1,5- and 1,8-dinitronaphthalene, chloronitrobenzenes, such as 2-chloro-1,3- and 1-chloro-2,4-dinitrobenzene, o-, m- and p-chloronitrobenzene and 1,2-dichloro-4-, 1,4-dichloro-2-, 2,4-dichloro-1- and 1,2-dichloro-3-nitrobenzene, chloronitrotoluenes, such as 4-chloro-2-, 4-chloro-3-, 2-chloro-4- and 2-chloro-6-nitrotoluene, nitroanilines, such as o-, m- and p-nitroaniline, nitroalcohols, such as tris (hydroxymethyl)nitromethane, 2-nitro-2-methyl- and 2-nitro-2-ethyl-1,3-propanediol, 2-nitro-1-butanol and 2-nitro-2-methyl-1-propanol, and any desired mixtures of two or more of said nitro compounds are preferably used in the novel process.

Aromatic nitro compounds, preferably mononitrobenzene, methylnitrobenzene or methylnitrotoluene, and in particular 2,4-dinitrotoluene or its industrial mixtures with 2,6-dinitrotoluene, these mixtures preferably comprising up to 35% by weight, based on the total mixture, of 2,6-dinitrotoluene with from 1 to 4 percent of vicinal dinitrotoluene and from 0.5 to 1.5% of 2,5- and 3,5-dinitrotoluene, are preferably hydrogenated to the corresponding amines by the novel process. The novel process can be advantageously used in particular in the hydrogenation of dinitrotoluene isomers to the corresponding tolylenediamine derivatives (TDA).

The hydrogenation of aromatic amines can be carried out in the absence of a solvent or in solution. The solvents used are the substances customary for this purpose, in particular lower alcohols, preferably ethanol.

The novel hydrogenation is usually carried out in the presence of catalysts. Catalysts which may be used are the conventional and known hydrogenation catalysts.

Examples of these are metals of subgroup VIII of the Periodic Table of the Elements, which metals can be applied to support materials, such as active carbon or oxides of aluminum, of silicon or of other materials. Raney nickel and/or supported catalysts based on nickel, palladium and/or platinum are preferably used. It is also possible in principle to use homogeneous catalysts.

The novel process using heterogeneous catalysts can be carried out by the fixed-bed or suspension procedure. The fixed-bed procedure can be carried out by the liquid-phase or trickle-bed procedure.

In the suspension procedure, heterogeneous catalysts are likewise used. The preferred hydrogenation of nitro compounds to amines is likewise generally carried out in the presence of heterogeneous catalysts. The heterogeneous catalysts are generally used in a finely divided state and are suspended in finely divided form in the reaction suspension. Reactors used for the hydrogenation in suspension are in particular loop apparatuses, such as jet loops or propeller loops, stirred kettles, which may also be equipped as stirred kettle cascades, bubble columns or air-lift reactors.

The novel process is generally carried out under the reaction conditions customary for the specific reaction. Thus, the conversion of aromatic nitro compounds into aromatic amines is usually carried out at from 5 to 100, preferably from 10 to 50, bar and from 80 to 160° C., preferably from 80 to 150° C., in particular from 100 to 150° C.

In the novel process, the exchange surface between gas phase and liquid phase can, surprisingly, be substantially increased. The larger exchange surface makes it possible always to operate close to the saturation concentration of the hydrogen in the hydrogenation bath. Consequently, the probability that the free sites on the catalyst surface will be occupied by hydrogen molecules increases. This leads in turn to an increase in the yield and the selectivity of the process.

The novel process can be used without problems and without additional conversions in all existing hydrogenation reactors. The inert gases preferred for the novel process, in particular nitrogen, are available in sufficient quantitity at virtually all production locations.

A further advantage of the novel process is that expensive purification of the hydrogen used is no longer necessary. It is sufficient to remove from the hydrogen those components which act as a catalyst poison or which may lead to secondary reactions. This permits more economical hydrogen production.

The examples which follow illustrate the invention.

EXAMPLE 1 (COMPARISON)

A cylindrical reactor having an external circulation, a baffle plate in the lower reactor part and a concentric dip tube, as described in example 1 in WO 00/35852 was used. The reaction volume of the reactor was 0.05 m$^3$. The reactor was provided with 36 field tubes which were connected in parallel and altogether corresponded to a cooling area of about 2.5 m$^2$. The amount of cooling water fed into the field tubes was 1 m$^3$/h and the temperature of the cooling water fed into the field tubes was 30° C.

By means of a high-pressure pump, 40.3 kg/h of a dinitrotoluene melt, consisting of 80 parts by weight of 2,4-dinitrotoluene and 20 parts of 2,6-dinitrotoluene, was sprayed at 120° C. into a fast-flowing mixture of about 62 parts by weight of a corresponding diaminotoluene mixture, 36 parts by weight of water and 2 parts by weight of a finely divided nickel hydrogenation catalyst. By simultaneous introduction of 30 m$^3$ (S.T.P.)/h of hydrogen, a pressure of 25 bar was maintained in the reactor. In order to maintain the loop flow, a volume flow of 2.6 m$^3$/h was circulated in the external product circulation. A pressure of about 3 bar prevailed in the reaction nozzle, and the power supplied was 5 kW/m$^3$. The reaction took place under virtually isothermal conditions since the resulting heat of reaction was removed at the place of its formation. The maximum reaction temperature in the lower third of the reactor was 122° C. 26.7 kg/h of a corresponding diaminotoluene mixture and 15.8 kg/h of water were removed simultaneously and continuously from the reactor with retention of the catalyst, which corresponded to a space-time yield of 580 kg of amine mixture/m$^3$*h.

The purity of the hydrogen supplied was 99.99999% by volume at a discharge rate of from about 1 to 2%. The waste gas was separated with the aid of a condenser from the condensable fractions, which contained substantially steam, and was fed to the flare with a purity of over 99.5% by volume of hydrogen. No additional inert gases were fed in. The hydrogenation was operated at 120° C. and 26 bar absolute pressure. The amount by weight of water in the hydrogenation bath was about 35%.

The gas phase in the reactor was composed virtually exclusively of the steam from the water of reaction and the hydrogen. Thus, a total gas phase density of about 2.5 kg/m$^3$ can be calculated. On introduction of gas into the reactor with the aid of the nozzle and the internal circulation, it was possible to establish gas contents of not more than 10% by volume, based on the amount by volume of the gas in the hydrogenation bath, in the liquid phase of the reactor. Higher gas contents could not be achieved. By means of a reactor power balance, it was possible to determine from the measurements that the mean bubble diameter in the liquid phase of the reactor was about 7 mm.

EXAMPLE 2

The procedure was as in example 1, but 0.1 m$^3$ of nitrogen per 100 m$^3$ of hydrogen was additionally introduced via a bubbling line. The amount of waste gas of the reactor was regulated so that the purity of the discharged hydrogen after removal of the steam by condensation was only 90% by volume. There were no changes in the total pressure, the reactor temperature and the amount by weight of water in the hydrogenation bath in comparison with example 1. Assuming a completely back-mixed gas phase, the resulting total density of the gas in the reactor was thus about 4.4 kg/m$^3$, which is composed of the density of the nitrogen, of the hydrogen and of the steam. Measurements have subsequently shown that the gas content in the hydrogenation bath of the reactor increased, without further changes in the operation of the reactor, to 18% by volume, based on the amount by volume of gas in the hydrogenation bath. This is attributable only to a reduction in the bubble sizes. A power balance of the reactor showed that the mean diameter of the gas bubbles in the hydrogenation bath after the addition of nitrogen had decreased to about 4 mm.

EXAMPLE 3

A reactor as in example 1 was used. The fresh hydrogen was introduced into the reactor with a purity of 99.99% by volume. With a total added amount of 30 m$^3$ (S.T.P.)/h of hydrogen, 29.997 m$^3$ (S.T.P.)/h of hydrogen and 0.003 m$^3$ (S.T.P.)/h of inert gases were thus actually introduced. In order to ensure a hydrogen purity of at least 99% by volume in the gas phase of the hydrogenation reactor, it was necessary to discharge 1%, based on the amount of fresh gas, of waste gas. The waste gas then contained 0.297 m$^3$ (S.T.P.) of hydrogen and 0.003 m$^3$ (S.T.P.) of inert substances.

Starting from this operating state, the purity of the fresh hydrogen was reduced to 99.9% by volume. The effort involved in the production of the hydrogen decreased considerably as a result. If, as previously, 1% of waste gas (based on the amount of fresh gas) was discharged, i.e. 0.3 m³ (S.T.P.)/h left the reactor, this waste gas is composed of 0.27 m³ of H₂ and 0.03 m³ of inert substances. Consequently, the hydrogen purity in the waste gas after removal of the condensable fractions was about 90% by volume, which is in the particularly preferred range.

The advantage of this procedure is that less effort is involved in the purification of the fresh hydrogen, slightly less hydrogen is lost and there are smaller bubbles in the reactor, which provides a larger exchange surface.

EXAMPLE 4

The procedure was as in the initial state of example 3, but the amount of waste gas was reduced from 1% to 0.1%, based on the amount of fresh gas, and the composition of the fresh hydrogen was not changed. Thus, in absolute terms, only 0.03 m³/h of waste gas was discharged, said waste gas being composed of 0.027 m³/h of hydrogen and 0.003 m³/h of inert substances. The concentration of the hydrogen in the waste gas of the hydrogenation reactor was 90%.

The advantages of this variant are a substantially lower hydrogen loss and the larger mass transfer areas owing to smaller bubbles. The reactor requires absolutely no further modifications for this purpose, and all that is necessary is to further close the waste gas valve.

We claim:

1. A process for hydrogenating liquid organic compounds selected from the group of mononitrobenzene, methylnitrobenzene, methylnitrotoluene, 2,4-dinitrotoluene and mixtures of 2,4-dinitrotoluene and 2,6-dinitrotoluene, wherein hydrogen present in the reactor contains proportions of at least one gas which is inert in the hydrogenation reaction, said gas being selected from the group of nitrogen, noble gases and ammonia, and wherein the sum of the proportions of the gases which are inert in the hydrogenation reaction is from 3 to 50% by volume, based on the gas phase in the reactor.

2. A process as claimed in claim 1, wherein the sum of the proportion of the bases which are inert in the hydrogenation reaction is from 5 to 20% by volume, based on the gas phase in the reactor.

3. A process as claimed in claim 1, wherein the gas which is inert in the hydrogenation reaction is fed to the reactor as a mixture with the hydrogen.

4. A process as claimed in claim 1, wherein the gas which is inert in the hydrogenation reaction is fed into the reactor at a different point from the hydrogen.

5. A process as claimed in claim 1, wherein the content of gas which is inert in the hydrogenation reaction is established by regulating the amount of waste gas discharged from the reactor.

6. A process as claimed in claim 5, wherein the gas which is inert in the hydrogenation reaction is fed to the reactor as a mixture with the hydrogen.

7. A process as claimed in claim 2, wherein the gas which is inert in the hydrogenation reaction is fed to the reactor as a mixture with the hydrogen.

8. A process as claimed in claim 5, wherein the gas which is inert in the hydrogenation reaction is fed into the reactor at a different point from the hydrogen.

9. A process as claimed in claim 2, wherein the gas which is inert in the hydrogenation reaction is fed into the reactor at a different point from the hydrogen.

10. A process as claimed in claim 2, wherein the content of the gas which is inert in the hydrogenation reaction is established by regulating the amount of waste gas discharged from the reactor.

11. A process for hydrogenating liquid organic compounds selected from the group of mononitrobenzene, methylnitrobenzene, methylnitrotoluene, 2,4-dinitrotoluene and mixtures of 2,4-dinitrotoluene and 2,6-dinitrotoluene, wherein hydrogen present in the reactor contains proportions of at least one gas which is inert in the hydrogenation reaction, said gas being selected from the group of nitrogen, noble gases and ammonia, and wherein the gas which is inert in the hydrogenation reaction is fed to the reactor as a mixture with the hydrogen.

12. A process for hydrogenating liquid organic compounds selected from the group or mononitrobenzene, methylnitrobenzene, methylnitrotoluene, 2,4-dinitrotoluene and mixtures of 2,4-dinitrotoluene and 2,6-dinitrotoluene, wherein hydrogen present in the reactor contains proportions of at least one gas which is inert in the hydrogenation reaction, said gas being selected from the group of nitrogen, noble gases and ammonia, and wherein the gas which is inert in the hydrogenation reaction is fed into the reactor at a different point from the hydrogen.

13. A process as claimed in claim 11, wherein the sum of the proportions of the bases which are inert in the hydrogenation reaction is from 5 to 20% by volume, based on the gas phase in the reactor.

14. A process as claimed in claim 12, wherein the content of gas which is inert in the hydrogenation reaction is established by regulating the amount of waste gas discharged from the reactor.

* * * * *